United States Patent
Kim et al.

(10) Patent No.: US 9,962,417 B2
(45) Date of Patent: May 8, 2018

(54) *LACTOBACILLUS PLANTARUM* AND COMPOSITION CONTAINING SAME

(71) Applicant: CJ CHEILJEDANG CORP., Seoul (KR)

(72) Inventors: Bong Joon Kim, Incheon (KR); Heon Woong Jung, Seoul (KR); Ji Hoon Koh, Seoul (KR); Tae Jin Kim, Seoul (KR); Kang-Pyo Lee, Seoul (KR); Kwang Woo Hwang, Seoul (KR); Tae Joon Won, Seoul (KR)

(73) Assignee: CJ CHEILJEDANG CORP., Seoul (KR)

( * ) Notice: Subject to any disclaimer, the term of this patent is extended or adjusted under 35 U.S.C. 154(b) by 0 days. days.

(21) Appl. No.: 15/254,599

(22) Filed: Sep. 1, 2016

(65) Prior Publication Data

US 2017/0035815 A1 Feb. 9, 2017

Related U.S. Application Data

(63) Continuation of application No. 13/380,129, filed as application No. PCT/KR2009/004911 on Sep. 1, 2009, now Pat. No. 9,572,846.

(30) Foreign Application Priority Data

Jul. 14, 2009 (KR) .......................... 10-2009-0064091

(51) Int. Cl.

| | | |
|---|---|---|
| *A61K 35/747* | (2015.01) | |
| *A23K 10/18* | (2016.01) | |
| *C12R 1/25* | (2006.01) | |
| *A23L 33/135* | (2016.01) | |
| *C12N 1/20* | (2006.01) | |
| *A61K 35/00* | (2006.01) | |
| *A61Q 19/00* | (2006.01) | |
| *A61K 8/99* | (2017.01) | |

(52) U.S. Cl.
CPC ............ *A61K 35/747* (2013.01); *A23K 10/18* (2016.05); *A23L 33/135* (2016.08); *C12N 1/20* (2013.01); *C12R 1/25* (2013.01); *A23V 2200/304* (2013.01); *A23V 2200/324* (2013.01); *A23V 2200/3204* (2013.01); *A23Y 2220/67* (2013.01); *A61K 8/99* (2013.01); *A61K 2035/11* (2013.01); *A61K 2035/115* (2013.01); *A61K 2800/10* (2013.01); *A61Q 19/00* (2013.01)

(58) Field of Classification Search
CPC .... A61K 35/747; A61K 2035/11; A61K 8/99; A61K 2800/10; A61K 2035/115; C12N 1/20; A23K 10/18; A23L 33/135; C12R 1/25; A61Q 19/00; A23Y 2220/67; A23V 2200/324; A23V 2200/3204; A23V 2200/304

See application file for complete search history.

(56) References Cited

U.S. PATENT DOCUMENTS

| | | |
|---|---|---|
| 4,713,449 A | 12/1987 | Vanderslice |
| 2004/0047849 A1 | 3/2004 | Hsu et al. |
| 2006/0088513 A1 | 4/2006 | Inoue et al. |
| 2011/0312061 A1 | 12/2011 | Kim et al. |

FOREIGN PATENT DOCUMENTS

| | | |
|---|---|---|
| JP | 2006-519759 A | 8/2006 |
| KR | 10-1999-0008403 A | 1/1999 |
| KR | 10-2004-0023755 A | 3/2004 |
| KR | 2005080630 A | 8/2005 |
| KR | 10-2010-0063500 A | 6/2010 |
| KR | 10-2010-0063503 A | 6/2010 |
| KR | 10-1255050 A | 4/2013 |
| WO | WO 2007/108763 A1 | 9/2007 |
| WO | WO 2010/064777 A1 | 6/2010 |

OTHER PUBLICATIONS

Ngo, ST et al. Gender differences in autoimmune disease. Fronteirs in Neuroendocrinology. 2014. 35: 347-369.*
Mosmann, TR et al. The expanding universe of T-cell subsets: Th1, Th2 and more. Immunology Today. 1996. 17(3): 138-146. (Year: 1996).*
Disis, ML et al. Immune regulation of cancer. Journal of Clinical Oncology. 2010. 28(2): 4531-4538. (Year: 2010).*
Maizels, RM et al. Immune regulation by helminth parasites: Cellular and molecular mechanisms. Nature Reviews Immunology. 2003. 3: 733-744. (Year: 2003).*
Lawrence, CE et al. IL-4-regulated enteropathy in an intestinal nematode infection. Eur. J. Immunol. 1998. 28: 2672-2684. (Year: 1998).*
Elenkov et al., "Stress Hormones, Th1/Th2 patterns, pro/anti-inflammatory cytokines and susceptibility to disease", TEM., 10(9):359-368, (1999).
Hirose et al., "Daily Intake of Heat-Killed Lactobacillus plantarum L-137 Augments Acquired Immunity in Healthy Adults", Journal of Nutrition, 136:3069-3073 (2006).
KR2005080630 Derwent Abstract, 2 pages, Aug. 2005.
Won et al., "Modulation of Th1/Th2 balance by Lactobacillus strains isolated from kimchi via stimulation of macrophage cell line J774A.1 in vitro", Journal of Food Science, 76(2):H55-H61, Published online Mar. 1, 2011 (2011).

* cited by examiner

*Primary Examiner* — Renee Claytor
*Assistant Examiner* — Susan E. Fernandez
(74) *Attorney, Agent, or Firm* — Birch, Stewart, Kolasch & Birch, LLP

(57) ABSTRACT

The present invention provides *Lactobacillus plantarum* CJLP55 KCTC 11401BP, a composition for treating bowel disease containing the *lactobacillus*, and a composition for immunological enhancement containing the *lactobacillus*.

12 Claims, 9 Drawing Sheets

LACTOBACILLUS PLANTARUM AND COMPOSITION CONTAINING SAME

CROSS-REFERENCE TO RELATED APPLICATIONS

This application is a Continuation of copending application Ser. No. 13/380,129 filed on Dec. 22, 2011, which is the U.S. National Phase of International Application No. PCT/KR2009/004911, filed Sep. 1, 2009, and which claims priority to Application No. 10-2009-0064091 filed in Korea, on Jul. 14, 2009. The entire contents of all of the above applications is hereby incorporated by reference.

FIELD OF THE INVENTION

The present invention relates to a novel *Lactobacillus plantarum* and a composition comprising the same. More particularly, the present invention relates to a novel *Lactobacillus plantarum* useful in the prevention and treatment of an enteropathy and an immune disease and a composition comprising the same.

BACKGROUND OF THE INVENTION

Lactic acid bacteria are abundantly present in fermented foods such as Kimchi and usually dwell in the digestive tract with a function of degrading fibroid materials and composite proteins into useful metabolites. As such, live microorganisms of a benefit to the host by improving the microbial environment in the gut are collectively designated as probiotics. To function as probiotics, microorganisms must reach the intestine alive after oral uptake and must stay on intestinal surfaces adhered. Therefore, they are fundamentally required to have excellent acid- and bile acid-resistance and ability to adhere to intestinal epithelial cells.

*Lactobacillus* sp. microorganisms are representative probiotics microorganisms which are abundantly present in Korean conventional fermented foods such as Kimchi. *Lactobacillus* sp. microorganisms are homo- or hetero-fermentative lactic acid bacilli which can be readily found in gut of animals including a human being or in the fermentation process of diary products or vegetables. *Lactobacillus* sp. microorganisms are known to have the beneficial functions of vitamin synthesis, anticancer activity and blood cholesterol reduction in addition to maintaining a pH of intestines acidic, inhibiting the excessive growth of harmful bacteria such as *E. coli* or *Clostridium* and improving condition of diarrhea and constipation. It has been reported that Acidophilin which is produced by lactic acid bacilli can inhibit the growth of dysentery *bacilli, salmonella, staphylococci, E coli* and so on. Further, it can stop diarrhea by suppressing the growth of diarrhea-causing bacteria and normalizing the intestinal microfloral environment (Michael and Philippe, Probiotics and prebiotics: Effects on diarrhea, The journal of nutrition, Volume 137, March 2007, pages 803S-811S ; Roberfroid, Prebiotics and probiotics: Are they functional foods?, American journal of clinical nutrition, Volume 71, June 2000, pages 1682S-1687S).

Researches have been intensively made to develop the *Lactobacillus* sp. microorganisms as probiotic agents and animal feeds by taking advantage of the above properties of *Lactobacillus* sp. microorganisms. Bacterial diarrhea causes livestock to lose weight or even die. To increase productivity of livestock by preventing the onset of the disease, antibiotics have been generally added to the feedstock of livestock. However, use of antibiotics in animal feeds has been regulated and organic methods of raising livestock have been recommended because of problems such as advent of resistant bacteria and antibiotics residues within livestock products (Korean Patent Laid-Open Publication No. 1998-78358) (McEwen and Fedorka-Cray, Antimicrobial use and resistance in animals, Clinical infectious Diseases, Volume 34, June 2002, pages S93-S106).

In addition, lactic acid bacteria such as *Lactobacillus* sp. microorganisms are known as exhibiting immunopotentiating activity. Possibly because of worldwide environmental pollution and instant food-uptake increase, allergic and atopic diseases associated with abnormal immunomodulation have increased rapidly over the world including Korea. Recently, an attempt to treat or alleviate diseases by bacteriotherapy in which pathogenic microorganisms are displaced with beneficial bacteria by the oral administration of lactic acid bacteria has been made in Europe. It has been reported that incidence rate of atopic diseases in infants decreased to about half the level by administration of *Lactobacillus rhamnosus* GG (Kalliomaki et. al., Probiotics in primary prevention of atopic disease: a randomized placebo-controlled trial, Lancet, Volume 357, April 2001, pages 1076-1079) and that area and severity of progressive atopic eczema in children decreased by administration of *Lactobacillus* rhamnosus and *Lactobacillus reuteri* (Rosenfeldt et. al., Effect of probiotic *Lactobacillus* strains in children with atopic dermatitis, Dermatologic and ocular diseases, Volume 111, February 2003, pages 389-395).

The immunopotentiating mechanism of lactic acid bacteria has been steadily studied. Although the underlying mechanism has not been clearly identified, it is generally known that lactic acid affects gastrointestinal tract immune system through oral introduction and existence in the gastrointestinal tract. For example, it has been reported that the uptake of lactic acid bacteria with yogurt increases the antibacterial activity of Peyer's patch's lymphocytes. And, tests with animals and humans showed that lactic acid bacteria potentiate the response of IgA. Further, lactic acid bacteria have an influence on both innate immunity and adaptive immunity. It is known that in innate immunity of the intestinal immune system, lactic acid bacteria defend health against infection by recognizing and killing pathogens. Further, it is known that in adaptive immunity, lactic acid bacteria activate macrophages which functions in phagocytosis of pathogens and presentation of antigens to T lymphocyte, resulting in that production of various cytokines, inter alia, IL12 and IL-18 is increased. In this regard, it is known that some of the constituents of the cell wall of lactic acid bacteria activate the NF-κB and STAT signaling pathway in macrophages and thereby stimulate the production of cytokines. In addition, lactic acid bacteria increase the production of IL-12, IL-18 and TNF-α in dendritic cells, which are specialized antigen-presenting cells abundantly found in the lymph nodes and the mucosa of the digestive tract, as well as the expression of T-lymphocyte-activating surface molecules such as MHC class II and 87-2 (Cross et. al., Anti-allergy properties of fermented foods: an important immunoregulatory mechanism of lactic acid bacteria?, International Immunopharmacology, Volume 1, May 2001, pages 891-901).

T lymphocytes play a central role in adaptive immunity. Adaptive immunity is categorized into a Th1 response leading to cell-mediated immunity and a Th2 response leading to humoral immunity. The cytokines produced by antigen-presenting cells are different between the Th1 response and Th2 response. IL-12, IL-18 and interferon (EFN) are predominantly produced in the Th1 response whereas PGE2, IL-4, and IL-10 are predominantly produced in the Th2 response. For immune system homeostasis, the Th1 and Th2 responses should keep the balance. The disruption of Th1/Th2 balance gives rise to immune disorders. Generally, Th1 cells are more effective against infection, while Th2 cells are responsible mainly for allergic and inflammatory responses. When acting normally, Th2 cells protect the body from dust and other undesired substances. When excessively activated, Th2 cells induce the hyperproduction of IgE antibodies, giving rise to allergic reactions to proteins which are not normally antigenic (e.g., pollen, foods). Therefore, Th1 responses must be in balance with Th2 responses and a surplus or deficiency of either of them causes diseases. Chronic stress induces the continuous release of cortisol, which causes a decrease in Th2 response but an increase in Th1 response, resulting in the induction of cancer, atopy, allergy, and autoimmune diseases (lenkov and Chrousos, Stress hormones, Th1/Th2 patterns, pro/anti-inflammatory cytokines and susceptibility to disease, Trends in Endocrinology and Metabolism, Volume 10, November 1999, pages 359-368).

It is reported that, in vivo, lactic acid bacteria stimulate the production of the Th1 cytokine IFN-γ, but suppress the release of the Th2 cytokines IL-4 and IL-5 in T lymphocytes (Matsuzaki et. al., The effect of oral feeding of *Lactobacillus casei* strain Shirota on immunoglobulin E production in mice, Journal of Dairy Science, Volume 81, January 1998, pages 48-53). According to another experiment, when ovalbumin-primed mice showing a Th2 bias were administered orally with lactic acid bacteria, the IFN-γ level of the splenocytes increased but the IL-4, IL-5 and IgE levels decreased. Further, the incubation of the splenocytes isolated from ovalbumin-primed mice with a Th2 bias, together with lactic acid bacteria, brought about a change in cytokine and IgE levels in agreement with the results of the oral administration experiment. However, because the incubation of only T lymphocytes together with lactic acid bacteria did not lead to a significant increase in IFN-γ level, it seems that antigen-presenting cells such as macrophages and dendritic cells are required for for the IFN-γ production of T lymphocytes (Kato et. al., Lactic acid bacterium potently induces the production of interleukin-12 and interferon-gamma by mouse splenocytes, International Journal of Immunopharmacology, Volume 21, February 1999, pages 121-131). IL-12 and IL-18, both of which are cytokines playing an important role in differentiating Th0 lymphocytes into Th1 lymphocytes, are produced in macrophages or dendritic cells. When treated with lactic acid bacteria in incubation, splenocytes or microphages are known to increase the production of IL-12, IL-18 and IFN-α in dose-dependent manners. As such, lactic acid bacteria increases the production of 1L-12, IL-18 and IFN-α in macrophages, thus promoting differentiation into Th1 cells with the concomitant induction of IFN-γ production, so that they can act to drive a Th2-predominant condition toward a Th1/Th2 balance (Cross et. al., Anti-allergy properties of fermented foods: an important immunoregulatory mechanism of lactic acid bacteria?, International Immunopharmacology, Volume 1, May 2001, pages 891-901). Therefore, it is reported that lactic acid bacteria are useful in the prevention or treatment of immune diseases such as cancers, atopy, allergy and autoimmune diseases, which are caused by the disruption of the Th1/Th2 balance triggered by an excessive Th2 response.

SUMMARY OF THE INVENTION

Figure 1:
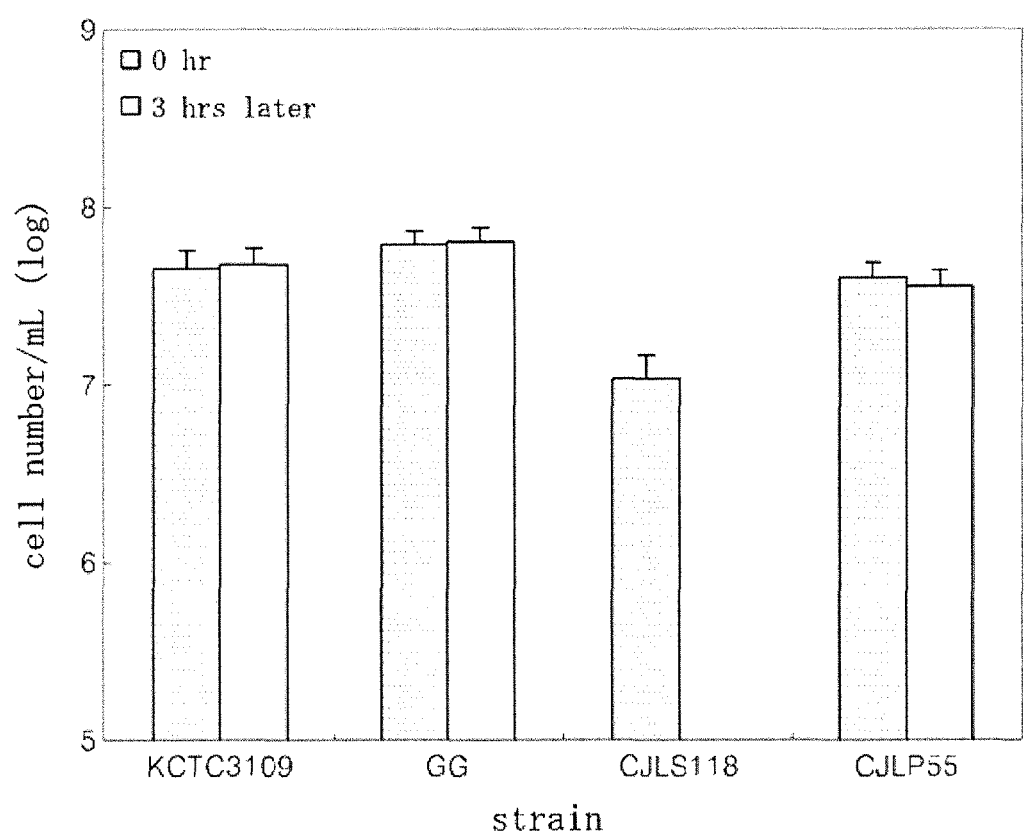
FIG. 1 is a graph showing the acid resistance of *Lactobacillus plantarum* CJLP55.

The present inventors conducted an intensive and thorough research into probiotics in order to develop novel lactic acid bacteria with an excellent modulatory effect on Th1/Th2 imbalance resulting from surplus Th2 responses over prior lactic acid bacteria. As a result, the present inventors found that a novel *lactobacillus* sp. strain isolated from Korean traditional fermented foods has the above effects.

It is therefore an object of the present invention to provide a novel *Lactobacillus* sp. strain useful as a probiotic which has an excellent immunopotentiating effect, particularly an immunomodulatory effect on the Th1/Th2 imbalance in favor of a Th2 shift as well as excellent acid- and bile acid-resistance and adhesion to intestinal epithelial cells.

It is another object of the present invention to provide a composition for the prevention or treatment of enteropathy, comprising the novel *Lactobacillus* sp. strain.

It is a further object of the present invention to provide an immunopotentiating composition comprising the novel *Lactobacillus* sp. strain.

In order to accomplish the above objects, the present invention provides *Lactobacillus plantarum* CJLP55 (deposited with the Korean Collection for Type Cultures on Oct. 16, 2008, with accession No. KCTC 11401BP): deposited at: Korea Research Institute of Bioscience and Biotechnology (KRIBB), 111 Gwahangno, Yuseong-gu, Daejeon 305-806, Republic of Korea).

In addition, the present invention provides a composition for the prevention or treatment of enteropathy, comprising *Lactobacillus plantarum* CJLP55.

Further, the present invention provides an immunopotentiating composition comprising *Lactobacillus plantarum* CJLP55.

A detailed description will be given of the present invention, below.

DETAILED DESCRIPTION OF THE INVENTION

*Lactobacillus plantarum* CJLP55 according to the present invention is a novel strain of *Lactobacillus* plantarum which was isolated and identified from Korean traditional fermented foods. Examples of the traditional fermented foods include, but are not limited to, Kimchi, vegetable ferments, fermented soybean paste, soy source, fast-fermented soybean paste, and salted seafoods.

For identification and classification thereof, the novel strain according to the present invention was subjected to 16S rRNA base sequencing. As a result, it was found to have the highest molecular phylogenetic relationship with the reference strain *Lactobacillus plantarum* (*Lactobacillus plantarum* NBRC15891$^T$, GenBank accession number AB326351) due to the highest homology (99.9%) therebetween. Therefore, the novel strain was identified as a strain of *Lactobacillus* plantarum, named *Lactobacillus* plantarum CJLP55, and deposited with the Korean Collection for Type Cultures on Oct. 16, 2008 (accession number KCTC 11401BP). The nucleotide sequence of 16S rRNA of *Lactobacillus plantarum* CJLP55 is represented by SEQ ID NO.1 as given in the following sequence list text.

*Lactobacillus plantarum* CJLP55 is Gram positive and facultative anaerobic so that it can grow both aerobically and anaerobically. The novel bacteria do not form a spore nor move, and has a rod shape. More concrete morphological and physiological properties of *Lactobacillus plantarum* CJLP55 were analyzed using well-known methods in the art and the results are summarized in following Table 1.

TABLE 1

| Morphological, Physiological and Biochemical Properties | Results |
| --- | --- |
| Morphology *Bacillus* | Rod |
| Motility | − |
| Spore | − |
| Catalase | − |
| Homo-hetero fermentation | Facultative heterofermentation |
| Proliferation at 15° C. | + |
| Proliferation at 45° C. | − |
| Proliferation at 3% NaCl | + |
| Anaerobic growth | + |
| Formation of CO2 using glucose | − |
| Sugar fermentation | |
| Glycerol | − |
| Erythritol | − |
| D-arabinose | − |
| L-arabinose | − |
| Ribose | + |
| D-xylose | − |
| L-xylose | − |
| Adonitol | − |
| Xyloside | − |
| Galactose | + |
| D-glucose | + |
| D-fructose | + |
| D-mannose | + |
| L-sorbose | − |
| Rhamnose | + |
| Dulcitol | − |
| Inositol | − |
| Mannitol | + |
| Sorbitol | + |
| D-mannoside | − |

TABLE 1-continued

| Morphological, Physiological and Biochemical Properties | Results |
| --- | --- |
| D-glucoside | − |
| Glucosamine | + |
| Amygdalin | + |
| Albutin | + |
| Esculin | + |
| Salicin | + |
| Cellobiose | + |
| Maltose | + |
| Lactose | + |
| Melibiose | + |
| Saccharose | + |
| Trehalose | + |
| Inulin | + |
| Melizitose | + |
| D-raffinose | + |
| Amidon | − |
| Glycogen | − |
| Xylitol | − |
| Gentiobiose | + |
| D-turanose | − |
| D-lyxose | − |
| D-tagatose | − |
| D-fucose | − |
| L-fucose | − |
| D-arabitol | − |
| L-arabitol | − |
| Gluconate | − |
| 2-gluconate | − |
| 5-gluconate | − |

+: positive
−: negative

For long-term storage, preferably, the inventive novel strain *Lactobacillus plantarum* CJLP55 may be cryopreserved with a storage solution prepared from a mixture of water and glycerol at −70° C. or may be suspended in sterile 10% skim milk before lyophilization.

Also, the inventive novel strain *Lactobacillus plantarum* CJLP55 serves as probiotics that show the activities of general gastrointestinal protection and immunopotentiation.

As used herein, the term "probiotic" is understood to be a live microorganism that benefits the health on the host by improving the microbial environment in the gastrointestinal tract of animals including a human being. Probiotics, that is, live microorganisms with probiotic activity, may be single or composite strains and may beneficially affect intestinal flora in the host after uptake thereof in the form of dried cells or fermented products. To serve as probiotics, microorganisms must pass through the stomach into the intestine in a living state and have a tolerance to gastric and bile juice. Also, they must settle down and inhabit the intestine and have a beneficial influence on intestinal microflora. Therefore, firstly, they should be resistant to gastric juice and bile acid and also be able to adhere to intestinal epithelial cells. Next, the microorganisms must be safe to the body. In this regard, a gelatin liquefaction test, a phenylalanine deaminase test, an ammonia formation test, and a hemolysis test are generally conducted. *Lactobacillus plantarum* CJLP55 according to the present invention was observed to be negative to the gelatin liquefaction test, the phenylalanine deaminase test, and the ammonia formation test, as well as to show excellent tolerance to acid and bile acid and ability to adhere to intestinal epithelial cells. Also, a-hemolysis was observed, indicating that *Lactobacillus plantarum* CJLP55 is not pathogens.

Considering its excellent acid- and bile acid-resistance and ability of adhering to intestinal epithelial cells, *Lactobacillus plantarum* CJLP55 according to the present invention is anticipated to have excellent gastrointestinal protecting effects. Therefore, in accordance with another aspect thereof, the present invention provides a composition for preventing or treating intestinal diseases, comprising *Lactobacillus plantarum* CJLP55.

The composition for prevention or treatment of enteropathy which comprises the inventive microorganism may be useful for the prevention or treatment of intestinal diseases of mammals including humans, such as livestock, e.g., cattle, horses, and pigs. The term "enteropathy or intestinal diseases," as used herein, is intended to refer to enteral infections with harmful bacteria or inflammatory bowel diseases. Examples of the intestinal diseases include, but are not limited to, infectious diarrhea caused by pathogenic microorganisms (*E. coli, salmonella*, and *clostridium*), gastroenteritis, inflammatory bowel diseases, psychogenic enteritis syndrome, overgrowth of microorganisms in the small intestine, diarrhea, and the like. *Lactobacillus plantarum* CJLP55 contained in the composition for preventing or treating intestinal diseases may be alive or dead, and preferably alive. In general, live bacteria have an ability to treat or improve general symptoms caused by the abnormal fermentation of intestinal flora, to prevent harmful bacteria from adhering to the intestinal tracts in humans and animal when they inhabit the intestinal tracts, and to produce lactic acid, thereby lowering the intestinal pH and suppressing proliferation of harmful bacteria. In addition, the administered live bacteria produce bacteriocin and peroxides to suppress the proliferation of pathogens and promote the activity of intestinal villi to absorb nutrients. Further, live bacteria may produce materials which are helpful for the absorption and utilization of nutrients, improve animal feed requirements, and generate materials neutralizing the toxic materials of pathogens.

The composition for the prevention or treatment of intestinal diseases in accordance with the present invention may be preferably orally administered, but the method of administering the composition is not limited thereto. The dose may vary depending on various factors including the type and severity of intestinal diseases, the age, gender and ethnicity of patients, and the purpose of prevention. Typically, the bacteria may be administered in an amount of from 10 million to 100 billion cells a day to an adult.

In addition to the gastrointestinal protecting effect, *Lactobacillus plantarum* CJLP55 of the present invention has an excellent immunopotentiating effect compared to conventional lactic acid bacteria. *Lactobacillus plantarum* CJLP55 is found to promote the production of IL-12 leading to a Th1 response, but suppress the production of IL-4 leading to Th2 responses in splenocytes. Further, the inventive novel strain stimulates immunomodulatory cells such as macrophages and dendritic cells, which are antigen-presenting cells capable of modulating the immune responses of T cells, to produce cytokines that induce Th0 lymphocytes to differentiate into Th1 lymphocytes, thus driving the Th2-shifted Th1/Th2 imbalance toward Th1 responses. A detailed description of the immunopotentiating effect of *Lactobacillus plantarum* CJLP55 is now given as follows.

When the mouse splenocytes which were allowed to shift toward Th2 responses by the administration of ovalbumin (OVA) were treated with *Lactobacillus plantarum* CJLP55, *Lactobacillus plantarum* CJLP55 induced the production of IL-12, a cytokine leading to Th1 response, at a level 12.4 12.7 times as high that of a negative control and suppressed the production of IL-4, a cytokine leading to Th2 response, at a level of 6.1-9.8% as high as that of the negative control. It means that the inventive novel strain has significant advantages in terms of the immunomodulative activity over other typical lactic acid bacteria *Lactobacillus rhamnosus*GG (KCTC 5033), *Lactobacillus casei* (KCTC 3109) and *Lactobacillus sakei* CJLS118 (KCTC13416). Therefore, *Lactobacillus plantarum* CJLP55 is highly immunomodulative such that it promotes Th1 responses with the concomitant suppression of Th2 responses, to modulate the Th1/Th2 imbalance in favor of a Th2 shift.

It was found that the number of lactic acid bacteria increased and the immunopotentiating activity of *Lactobacillus plantarum* CJLP55 was enhanced in the microphage cell line RAW264.7 and the dendritic cell line JAWSII which were cultured together with the inventive novel strain. When the microphage cell line RAW264.7 and the dendritic cell line JAWSII were treated with *Lactobacillus plantarum* CJLP55, production of IL-12 and IL-18 which are cytokines inducing differentiation into Th1 was stimulated and IL-10 which is a cytokine inhibiting differentiation into Th1 was less produced than IL-12, thereby differentiation into Th1 being promoted. It was also understood from these results that *Lactobacillus plantarum* CJLP55 has an immunomodulatory activity of modulating a Th2-shifted Th1/Th2 imbalance by promoting Th1 responses and suppressing Th2 responses.

IL-4 is produced by Th2 cells and plays a central role in specific cell-mediated immunity. It also has a function of an anti-inflammatory cytokine, that is, it inhibits the production of IL-12, a cytokine of Th1 cells. Recently, it has been reported that the peripheral blood and skin lesions of atopic dermatitis patients are relatively increased in Th2 cells, which are responsible mainly for the production of IL-4 and IL-5 (Miraglia et. al, Immune dysregulation in atopic dermatitis, Allergy and Asthma Proceedings, Volume 27, November-December 2006, pages 451-455). Thus, a Th1/Th2 imbalance in favor of Th2-mediated immune responses induces diseases such as atopic dermatitis. In addition, as described above, a surplus or deficiency of Th1 or Th2 over the other causes the outbreak of diseases. For example, it is known that a relative decrease in Th1 response or a relative increase in Th2 response induces the onset of immune cell-mediated diseases such as cancers, atopic diseases, allergies and autoimmune diseases (Elenkov and Chrousos, Stress hormones, Th1/Th2 patterns, pro/anti-inflammatory cytokines and susceptibility to disease, Trends in Endocrinology and Metabolism, Volume 10, November 1999, pages 359-368). Thus, it is expected that *Lactobacillus plantarum* CJLP55 can be applied to the prevention or treatment of atopic diseases and allergies as well as cancers and autoimmune diseases by modulating the production of cytokines from immunmodulatory cells such as Th1, Th2, macrophages and dendritic cells to drive a Th2-shifted Th1/Th2 imbalance toward Th1 responses.

In accordance with another aspect thereof, the present invention provides an immunopotentiating composition comprising *Lactobacillus plantarum* CJLP55. The immunopotentiating composition of the present invention has an immunopotentiating effect because *Lactobacillus plantarum* CJLP55 is a lactic acid bacterium that is effective for enhancing immune response as described above. Particularly, as will be proven in the following Example Section, the immunopotentiating composition of the present invention is effective at preventing or treating diseases caused by a Th1/Th2 imbalance in favor of a Th2 shift, because *Lactobacillus plantarum* CJLP55 can promote Th1 responses and modulate the Th1/Th2 imbalance. Thus, the immunopotentiating composition of the present invention may be effectively used to prevent or treat atopic disease, allergies, cancer and autoimmune disease. The autoimmune diseases include asthma and hay fever, but are not limited thereto.

The immunopotentiating composition of the present invention may be orally administered, but administration method is not limited thereto. The dose may vary depending on various factors including the type of the disease requiring immunopotentiation, the severity of the disease, the age, gender and ethnicity of patients, and the purpose of treatment or prevention. In general, the bacteria are administered in an amount of 10 million to 100 billion cells a day to an adult.

The composition for preventing and treating enteropathy or the immunopotentiating composition, both of which comprise the inventive *Lactobacillus plantarum* CJLP55 according to the present invention proven safe, can be applied to pharmaceuticals, foods, cosmetics, animal feeds or animal feed additives, without any concern about side effects.

When applied to pharmaceuticals, the composition may be formulated into conventional pharmaceutical preparations known to the art. The pharmaceuticals may be prepared as oral dosage forms such as liquids, suspensions, powder, granules, tablets, capsules, pills or extracts.

Pharmaceutically acceptable excipients or additives suitable for formulations may be used. For example, formulations suitable for oral administration may include at least one carrier selected from the group consisting of a diluent, a lubricant, a binder, a disintegrating agent, a sweetener, a stabilizer and a preservative, and at least one additive selected from the group consisting of a flavoring agent, a vitamin and an antioxidant.

An arbitrary pharmaceutically acceptable excipient or additive may be used. Particularly, it is preferable to use lactose, corn starch, soybean oil, microcrystalline cellulose or mannitol as the diluent; magnesium stearate or talc as the lubricant; and polyvinyl pyrrolidone or hydroxypropylcellulose as the binder. In addition, it is preferable to use calcium carboxymethylcellulose, sodium starch glycolate, polacrilin potassium or crospovidone as the disintegrating agent; white sugar, fructose, sorbitol or aspartame as the sweetener; sodium carboxymethylcellulose, β-cyclodextrin, white wax or xanthan gum as the stabilizer; and methyl paraoxybenzoate, propyl paraoxybenzoate or potassium sorbate as the preservative.

In addition to the above substances, a natural flavor such as plum flavor, lemon flavor, pineapple flavor or herb flavor, a natural fruit juice, a natural colorant such as chlorophyllin or flavonoid, a sweetening agent such as fructose, honey, sugar alcohol or sugar, or an acidifier such as citric acid or sodium citrate, or combinations thereof may be added to the formulation in order to improve the taste.

Formulation techniques, and excipients and additives necessary for formulation are described in detail in Remington's Pharmaceutical Sciences (19th ed., 1995).

The composition of the present invention may also be used as a food. Among them are functional health foods and usual foods which humans take in widely and conventionally everyday. For use as a functional health food, the composition may be formulated into a variety of formulations that are commonly used in the art with sitologically acceptable excipients or additives. Examples of the functional health food include powder, granules, tablets, capsules, suspensions, emulsions, syrups, liquids, extracts, tea, jelly, drinks or the like. Any sitologically acceptable excipient or additive may be used so long as it is known as being usable in the art.

Because the composition of the present invention has preventive or therapeutic effects on atopic diseases, it may be used in cosmetics. If the composition of the present invention is used in cosmetics, it may be formulated into various cosmetic preparations that are commonly used in the art. When the composition is formulated, cosmetically acceptable excipients or additives may be added thereto.

The composition of the present invention may be used as a animal feed or a feed additive.

For use as a feed additive, the composition may be formulated into a liquid with a high concentration of from 20 to 90% or may be prepared as a powder or granules. The feed additive may include at least one selected from the group consisting of an organic acid such as citric acid, humalic acid, adipic acid, lactic acid or malic acid, a phosphate salt such as sodium phosphate, potassium phosphate, acidic pyrrophosphate or polyphosphate (polymerized phosphate), and a natural antioxidant such as polyphenol, catechin, a-tocopherol, rosemary extract, vitamin C, green tea extract, licorice extract, chitosan, tannic acid or phytic acid. If the composition is used as a animal feed, it may be formulated into conventional forms in the art with ingredients commonly used in animal feed.

The feed additive and animal feed may include grains such as powdered or pulverized wheat, oats, barley, corn or rice; plant protein animal feed containing rape, bean, or sunflower as a main ingredient; animal protein animal feed such as blood powder, meat powder, bone powder, or fish powder; sugar; and dairy products such as various powdered milk and whey powder. The feed additive and animal feed may further include nutrient supplements, digestion- and absorption-assisting agents, growth promoting substances or the like.

The animal feed additive may be administered alone or in combination with another edible excipient, to animals. In addition, the animal feed additive may be easily administered to animals as a top dressing to the animal feed or as a mixture with the animal feed, or in a separate oral form. If the feed additive is administered separately from the animal feed, it may be combined with a pharmaceutically acceptable edible vehicle to prepare an immediate release or sustained release formulation. The edible vehicle may be in a form of solid or liquid, such as corn starch, lactose, sucrose, bean flake, peanut oil, olive oil, sesame oil or propylene glycol. When a solid vehicle is used, the feed additive may be in the form of tablets, capsules, powder, troches or lozenges, or a non-dispersed top dressing. As for a liquid vehicle, the feed additive may be in the form of gelatin soft capsules, a syrup, a suspension, an emulsion or a solution.

The animal feed may include protein-containing organic cereal flour that is commonly used to satisfy the dietary demand of animals. The protein-containing cereal flour may comprise corn, bean flour or a corn/bean flour mix.

In addition, the feed additive and animal feed may include a supplement such as a preservative, a stabilizer, a wetting agent, an emulsifier, and a solubilizer. The feed additive may be added to the animal feed in an infiltration, spraying, or mixing manner.

The animal feed or feed additive may be applied to meals for various animals such as mammals, poultry and fish. The mammals include pigs, cows, sheep, goats, laboratory rodents and pets (e.g., dogs and cats). Examples of the poultry include chicken, turkeys, ducks, geese, pheasants and quails, and the fish includes trout, but are not limited thereto.

As described above, because *Lactobacillus plantarum* CJLP55 according to the present invention have excellent resistance to acid and bile acid and ability to adhere to intestinal epithelial cells, *Lactobacillus plantarum* CJLP55 according to the present invention can be used as a probiotic that provides effective gastrointestinal protection. Further, *Lactobacillus plantarum* CJLP55 promotes a Th1 response so that it is used to modulate a Th1/Th2 imbalance in favor of a Th2 shift. Therefore, *Lactobacillus plantarum* CJLP55 according to the present invention may be applied to a composition for treating intestinal diseases and an immunopotentiating composition. Particularly, *Lactobacillus plantarum* CJLP55 is effective at treating diseases induced by a Th1/Th2 imbalance in favor of a Th2 shift.

A better understanding of the present invention may be obtained through the following examples which are set forth to illustrate, but are not to be construed as limiting the present invention.

EXAMPLE 1

Isolation and Identification of *Lactobacillus plantarum* CJLP55 Strains

*Lactobacillus plantarum* CJLP55 strains isolated from kimchi were smeared onto 1.5% agar MRS plates (Difco, USA), and incubated at 37° C. for 24 hours. Colonies that were proven to be pure were collected using a loop and incubated at 37° C. for 18 to 24 hours in a liquid MRS medium (Difco, USA).

Then, morphological and physiological properties of *Lactobacillus plantarum* CJLP55 strains were determined using a method reported by Kim et. al. (Kim et. al., *Leuconostoc inhae* sp. nov., a lactic acid bacterium isolated from kimchi, International Journal of Systematic and Evolutional Microbiology, Volume 53, July 2003, pages 1123-1126), and API5OCH and API5OCHL kits (Biomerio). The identified morphological and physiological properties of *Lactobacillus plantarum* CJLP55 are summarized in Table 1 above.

In addition, the base sequence of a 16S rRNA gene was analyzed in order to identify and classify lactic acid bacteria. The base sequence of 16S rRNA gene was determined and analyzed using the method of Kim et. al. (Kim et. al., *Leuconostoc kimchii* sp. nov., a new species from kimchi. International Journal of Systematic and Evolutional Microbiology, Volume 50, September 2000, pages 1915-1919). The determined base sequence of 16S rRNA gene of *Lactobacillus plantarum* CJLP55 is given in the sequence list text attached hereto (SEQ ID NO:1).

As a result of 16S rRNA base sequencing, the strain was found to have the highest homology (99.9%) with a *Lactobacillus plantarum* standard strain (*Lactobacillus plantarum* NBRC15891$^T$, GenBank accession number AB326351), and was identified to be a *Lactobacillus plantarum* strain and named *Lactobacillus plantarum* CJLP55, and deposited with the Korean Collection for Type Cultures on Oct. 16, 2008 (accession No.: KCTC11401BP).

EXAMPLE 2

Assay of *Lactobacillus plantarum* CJLP55 for Acid Resistance in Artificial Gastric Juice and Bile Acid Resistance in Artificial Bile Juice An acid resistance test was conducted with an artificial gastric juice prepared by a modified method of Kobayashi et. al., (Kobayashi et. al., Studies on biological characteristics of *Lactobacillus*: II. Tolerance of the multiple antibiotic resistance strain, *L. casei* PSR3002, to artificial digestive fluids. Japan Journal of Microbiology. Volume 29, July 1974, pages 691-697). In detail, the artificial gastric juice was prepared by adjusting the pH of a MRS broth to 2.5 with 1N HCl, adding pepsin in a concentration of 1000 unit/mL, and sterilizing the medium.

*Lactobacillus plantarum* CJLP55, isolated and identified in Example 1, was incubated in a MRS broth at 37° C. for 18 hours and centrifuged to precipitate into pellets of lactic acid bacteria. These were washed twice with sterilized saline (0.85% NaCl) and the cell suspension was inoculated onto a control medium and the artificial gastric juice to a concentration of about $10^7$ cfu/mL. During incubation at 37° C., viable cells were counted 0 and 3 hours after inoculation. The total count of the cells was measured by diluting the cells 10 times in a phosphate-buffered solution (pH 6.8) containing $KH_2PO_4$, $Na_2HPO$, L-cysteine, HCl and Tween 80.

A bile acid resistance test in artificial bile juice was performed using the method of Casey et. al. (Casey et. al., Isolation and characterization of anti *Salmonella* lactic acid bacteria from the porcine gastrointestinal tract, Letters in Applied Microbiology. Volume 39, 2004, pages 431-438). In this regard, *Lactobacillus plantarum* CJLP55 was incubated in a medium which was prepared by adding 0.3% bull bile to the MRS broth used in the acid resistance test above. The cells were inoculated in the same manner as in the acid resistance test above, and viable cells were counted 0, 12 and 24 hours after inoculation.

Further, the typical lactic acid bacteria strains *Lactobacillus casei* (KCTC 3109), *Lactobacillus sakei* CJLS118 (KCTC13416) and *Lactobacillus rhamnosus* GG (KCTC 5033) were subjected to the same acid- and bile acid-resistance tests as described above.

Figure 2:
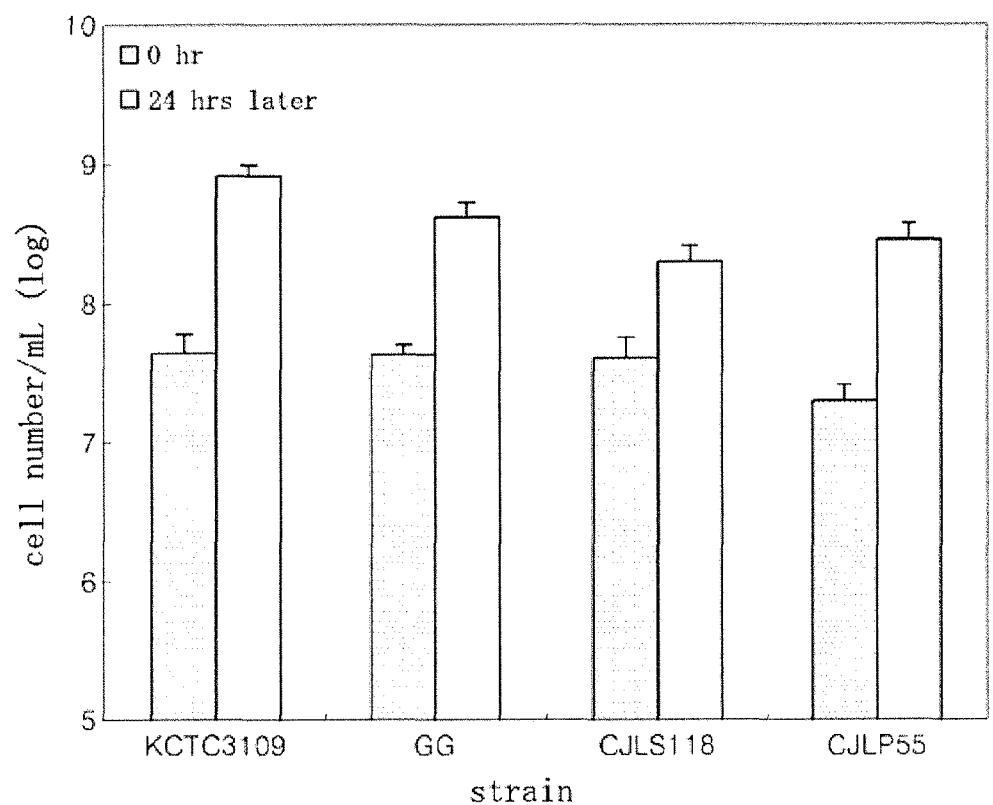
FIG. 2 is a graph showing the bile acid resistance of *Lactobacillus plantarum* CJLP55.

The results are shown in FIGS. 1 and 2. FIG.1 is a graph showing the acid resistance of *Lactobacillus plantarum* CJLP55. FIG. 2 is a graph showing the bile acid resistance of *Lactobacillus plantarum* CJLP55.

With reference to FIGS. 1 and 2, *Lactobacillus plantarum* CJLP55 had acid resistance and bile acid resistance which is equal to or greater than the comparative lactic acid bacteria strains. This result indicates that *Lactobacillus plantarum* CJLP55 of the present invention can reach the intestine alive without influence of gastric juice and survive with bile within the intestine.

EXAMPLE 3

Assay of *Lactobacillus* plantarum CAP55 for Ability to Adhere to Intestinal Epithelial Cells For use in a test for adhesion to intestinal epithelial cells, HT-29 was obtained from the Korean Cell Line Bank (KCLB), and the test was conducted using the methods of Kim et. al. (Kim et. al., Probiotic properties of *Lactobacillus* and *Bilidobacterium* strains isolated from porcine gastrointestinal tract, Applied Microbiology and Biotechnology, Volume 74, April 2007, pages 1103-1111) and of Hirano et al. (Hirano et. al., The effect of *Lactobacillus rhamnosus* on enterohemorrhagic *Escherichia coli* infection of human intestinal cells in vitro, Microbiology and Immunology, Volume 47,2003, pages 405-109). HT-29 cells were cultured in a RPMI 1640 (Gibco, USA) medium containing heat-inactivated 10% fetal bovine serum (FBS), 1% L-glutamine, penicillin G (100 IU/mL) and streptomycin (100 mg/mL) at 37° C. under a 5% $CO_2$ atmosphere. For assaying adhesion ability and adhesion inhibitory ability, first, HT-29 cells were seeded at a density of $1.0 \times 10^5$ cells/mL per well in 24-well plates and cultured with the replacement of the medium with a fresh one every other day until a complete monolayer was formed. The complete monolayer of HT-29 cells was washed five times with PBS buffer solution of 25° C., followed by the addition of 0.5 mL of an antibiotic-free RPMI 1640 medium thereto.

Lactobacillus plantarum CJLP55 was suspended in an RPMI medium to a concentration of about $1.0 \times 10^9$ cfu/mL, and the suspension was inoculated into the 24-well plates and incubated at 37° C. for 2 hours under a 5% $CO_2$ atmosphere. After the completion of incubation, the 24-well plates were washed three times with PBS buffer while stirring at 200 rpm for 3 min in order to remove the cells which remained unattached and to determine the adhesion ability over the washing. After washing, 0.2% trypsin-EDTA was added into the wells to detach the attached cells. The separated cells were diluted in peptone water in a serial dilution manner, smeared on MRS-agar plates and incubated at 37° C. for 24 hours. Thereafter, the cells were counted.

Separately, to identify partial adhesion, a cover glass completely sterilized by immersion in 70% alcohol for one day was placed on the bottom of a petri-dish before HT-29 cells were incubated therein, along with the same amount of lactic acid bacteria as described above. Lactic acid bacteria that were not washed off and remained adhering to the HT-29 cells were dried, Gram stained, observed under an optical microscope and counted. Lactobacillus sakei CJLS118 and Lactobacillus rhamnosusGG (KCTC 5033) were used for comparison in the same way.

Figure 3:
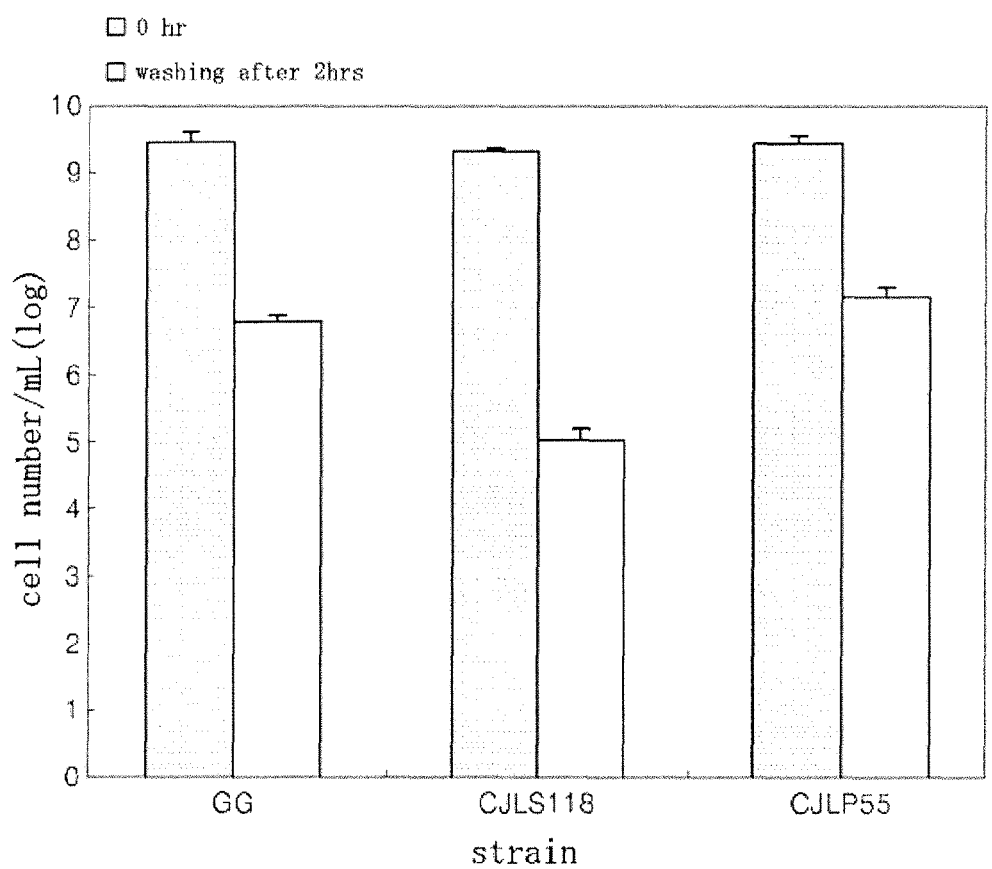
FIG. 3 is a graph showing an adhesion ability of *Lactobacillus plantarum* CJLP55 to intestinal epithelial cells.

The results are shown in FIG. 3. FIG. 3 is a graph showing the ability of Lactobacillus plantarum CJLP55 to adhere to intestinal epithelial cells.

Referring to FIG. 3, Lactobacillus plantarum CJLP55 was observed to have excellent ability to adhere to intestinal epithelial cells after 24 hours, compared to Lactobacillus rhamnosusGG (KCTC 5033) and Lactobacillus sakei CJLS118, both of which are commercially well known as a probiotics. Especially, Lactobacillus plantarum CJLP55 was observed to have the remarkably excellent ability compared to Lactobacillus sakeiCJLS118. These results imply that Lactobacillus plantarum CJLP55 according to the present invention is capable of adhering to intestinal epithelial cells and thus of improving the intestinal environment.

EXAMPLE 4

Safety Assessment of Lactobacillus plantarum CJLP55

In order to evaluate the safety of the strains isolated in Example 1, a hemolysis test, a gelatin liquefaction test, a harmful metabolite formation (ammonification) test, and a phenylalanine deaminase test were preformed using the safety test methods according to the standard of Korea Biotechnology Industry Organization.

The results are shown in Table 2 below.

Results of Safety assessment of Lactobacillus plantarum CJLP55 Strain

| | tests | | | |
|---|---|---|---|---|
| bacteria | gelatin liquefaction | phenylalanine deaminase | hemolysis | ammonification |
| CJLP55 | negative | negative | α-hemolysis, safe | negative |

According to the results, Lactobacillus plantarum CJLP55 was negative for the gelatin liquefaction test, the harmful metabolite (ammonia) formation test and the phenylalanine deaminase test, and showed a-hemolysis which is regarded as not being a pathogen. Thus, Lactobacillus plantarum CJLP55 was proven as being safely administered to the human body.

EXAMPLE 5

Assay for IL-12 Production in Treated Mouse Splenocyte

In order to assay the ability of Lactobacillus plantarum CJLP55 to promote the production of the Th1 response-inducing cytokine IL-12 in the splenocytes of ovalbumin-primed mice that showed a Th2 bias, the following experiment was conducted with reference to Fujiwara et al. (Fujiwara et. al. A double-blind trial of Lactobacillus paracasei strain KW3110 administration for immunomodulation in patients with pollen allergy, Allergology International, 2005, volume 54, pages 143-149) and Fujiwara et al. (Fujiwara et. al., The anti-allergic effects of lactic acid bacteria are strain dependent and mediated by effects on both Th1/Th2 cytokine expression and balance, International Archives of Allergy and Immunology, 2004, Volume 135, pages 205-215) as follows.

Immunization was performed as follows: 1.538 mL of 13 mg/mL alum hydroxide (Sigma), 10 mg of ovalbumin and 0.4615 mL of PBS were mixed well and were allowed to react for 20 min at room temperature. The resultant mixture was intraperitoneally injected into 5 subjects of 6-week-old female Balb/c mouse at a dose of 0.2 mL (1 mg OVA+2 mg alum) per mouse, followed by intraperitoneal injection at the same dose on the 6th day for boosting. The mice were sacrificed on the $13^{rd}$ day and the spleens were excised. The splenocytes thus obtained were plated in an amount of 100 μL ($4 \times 10^6$ cells/mL), along with 50 μL of dead cells of test and 50 μL of ovalbumin (4 mg/mL) into cell culture well plates and incubated for 7 days in DMEM-10 medium in a 10% $CO_2$ incubation. Thereafter, the supernatant was assayed for IL-12 level using an IL-12 ELISA kit (manufactured by Biosource).

The dead bacteria of the test were obtained as follows.

Bacteria of the test was inoculated into MRS broth (Difco) and cultured at 37° C. for 24 hours, followed by centrifugation at 13,000 rpm for 1 min to obtain cells as pellets. The cells were then washed twice with physiological saline and harvested. For an animal cell inoculation test, the bacterial cells were heated at 100° C. for 10 min in the same volume of sterilized distilled water as that of the original culture medium and harvested by centrifugation at 13,000 rpm for 1 min. After that, the cells were diluted in DMEM to form a concentration of 50 μg/mL and 5 μg/mL based on the cell culture medium. Lactobacillus plantarum CJLP55 was used as test bacteria. The same experiment was performed with Lactobacillus rhamnosus GG (KCTC 5033), Lactobacillus casei (KCTC 3109) and Lactobacillus sakei CJLS118 (KCTC 13416) for comparison.

The IL-12 assay was performed according to the instructions for the IL-12 ELISA kit. The O.D. values were measured in an ELISA reader and converted into the level of IL-12 according to linear regression for the IL-12 control sample supplied with the kit. The measurements are shown in FIG. 4.

Figure 4:
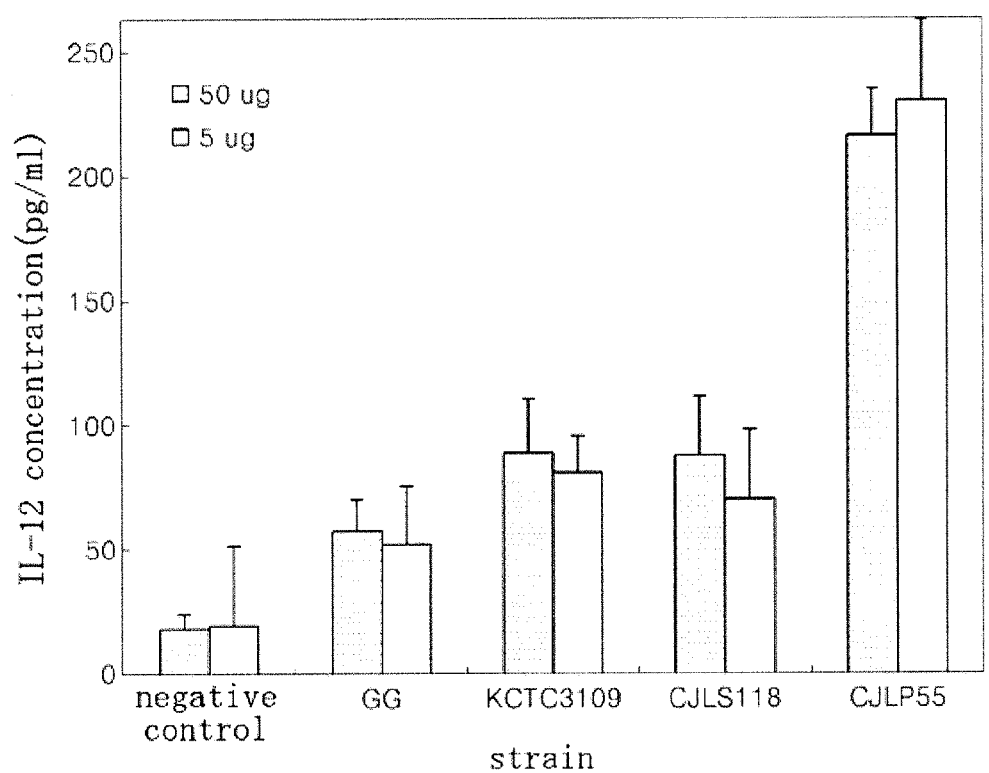
FIG. 4 is a graph showing the concentrations of the Th1 response-inducing cytokine IL-12 produced in the splenocytes of the ovalumin-primed and Th2 biased after treatment with *Lactobacillus plantarum* CJLP55 or other lactic acid bacteria.

FIG. 4 is a graph showing the concentrations of the Th1 response-inducing cytokine IL-12 produced in the splenocytes of ovalbumin-primed and Th2-biased mice, each of which were treated with Lactobacillus plantarum CJLP55 or other comparative lactic acid bacteria.

As is apparent from the data of FIG. 4, *Lactobacillus plantarum* CJLP55 was found to remarkably promote the production of the Th1 response-inducing cytokine IL-12, compared to the other lactic acid bacteria. Therefore, it was found that *Lactobacillus plantarum* CJLP55 according to the present invention significantly induced Th1 responses in the mice with a Th2 bias.

EXAMPLE 6

Assay for Inhibitory Activity Against IL-4 Production in Treated Mouse Splenocytes To assay the inhibitory activity of *Lactobacillus plantarum* CJLP55 against the production of the Th2 response-inducing cytokine IL-4 in the splenocytes of ovalbumin primed and Th2 biased mice, the same procedure and condition as in Example 5 were repeated, with the exception that an IL-4 kit (Biosource) was used instead of the IL-12 kit. The results are shown in FIG. 5.

Figure 5:
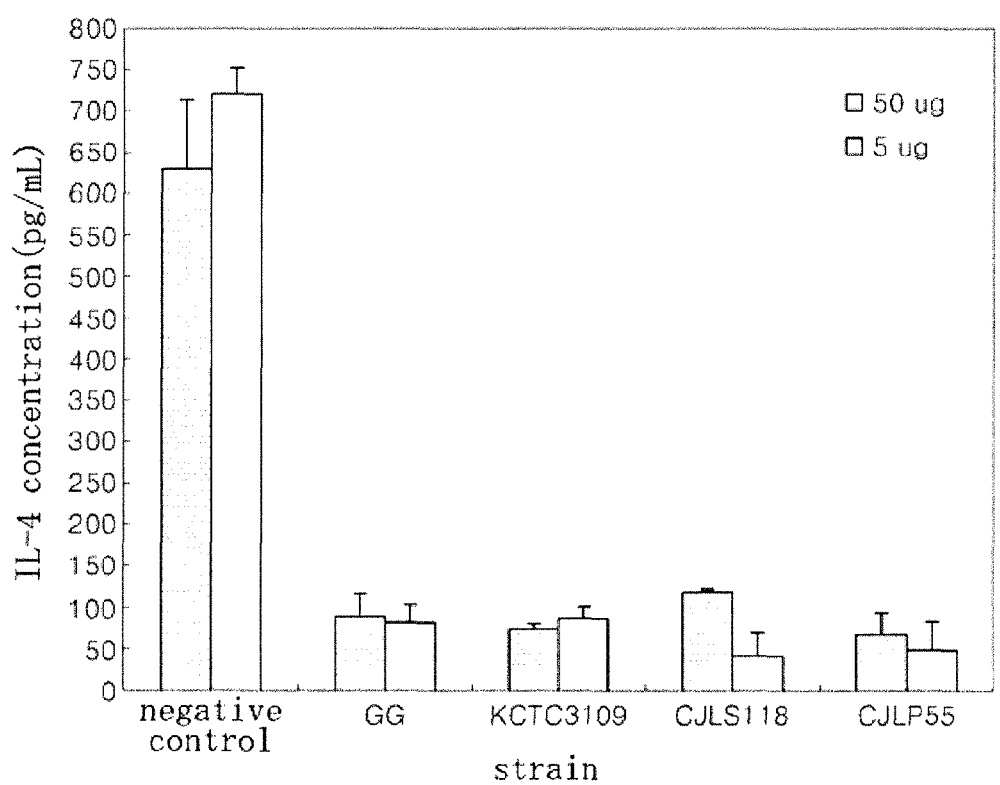
FIG. 5 is a graph showing the concentrations of of the Th2 response-inducing cytokine IL-4 produced in the splenocytes of the ovalumin-primed and Th2 biased mice after treatment with *Lactobacillus plantarum* CJLP55 or other lactic acid bacteria.

FIG. 5 is a graph showing the concentrations of the Th2 response-inducing cytokine IL-4 produced in the splenocytes of the ovalbumin primed and Th2 biased mice, each of which were treated with *Lactobacillus plantarum* CJLP55 or other comparative lactic acid bacteria.

As shown in FIG. 5, *Lactobacillus plantarum* CJLP55 was found to inhibit the production of the Th2 response-inducing cytokine IL-4 to suppress Th2-biased mouse splenocytes from mediating Th2 responses.

EXAMPLE 7

Assay for Expression of the Th1 Differentiation-Inducing CytokinesIL-12p40 and IL-18 and the Th1 Differentiation-Suppressing Cytokine IL-10 in Macrophage and Dendritic Cells Antigen-presenting cells (APCs) such as macrophages and dendritic cells produce IL-12 and IL-18, thereby inducing Th0 to differentiate into Th1. On the other hand, they produce IL-10, thereby suppressing Th0 differentiation into Th1. To evaluate the effect of the lactic acid bacteria of the present invention on the production of IL-12, IL-10 and IL-18 in macrophages and dendritic cells, an experiment was performed as follows.

Test bacteria cells were applied at a density of $5 \times 10^7$ cells/mL to the macrophage cell line RAW264.7 and, then, cultured at 37° C. for 48 hours in a 10% $CO_2$ incubator. The IL-12p40 and IL-10 levels of the supernatant were analyzed using ELISA.

The test bacteria were *Lactobacillus plantarum* CJLP55, with lipopolysaccharide serving as a positive control. The same test was performed on *Lactobacillus rhamnosus* GG (KCTC 5033), *Lactobacillus casei* (KCTC 3109) and *Lactobacillus sakei* CJLS118 (KCTC 13416) for comparison.

The concentrations were measured using an IL-12p40 kit (BD Biosciences, USA) for IL-12 and an IL-10 kit (BD Biosciences, USA) for IL-10 according to the instructions of the manufacturers. The results are shown in FIGS. 6 and 7, respectively.

Figure 6:
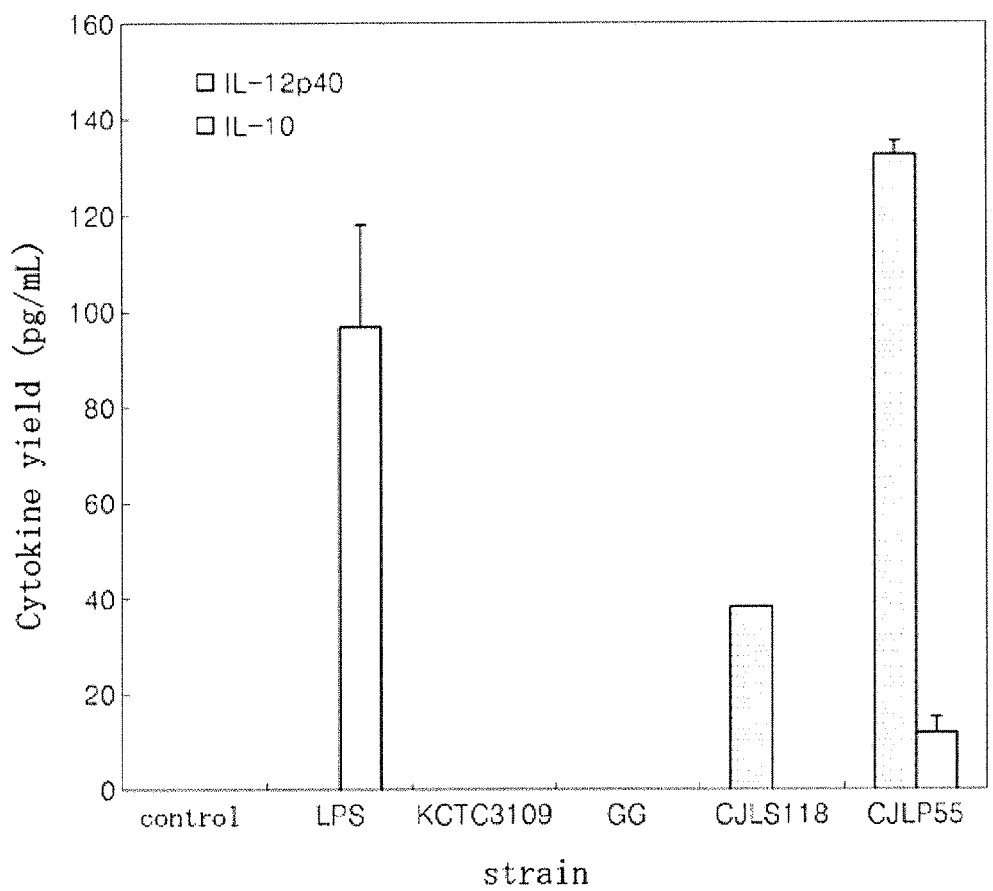
FIG. 6 is a graph showing the concentrations of IL-12 and IL-10 produced in the macrophage cell strain RAW264.7 treated with *Lactobacillus plantarum* CJLP55 or other lactic acid bacteria, as measured by ELISA.

FIG. 6 is a graph showing the concentrations of IL-12 and IL-10 produced in the macrophage cell strain RAW264.7 treated with *Lactobacillus plantarum* CJLP55 or other references, as measured by ELISA.

Figure 7:
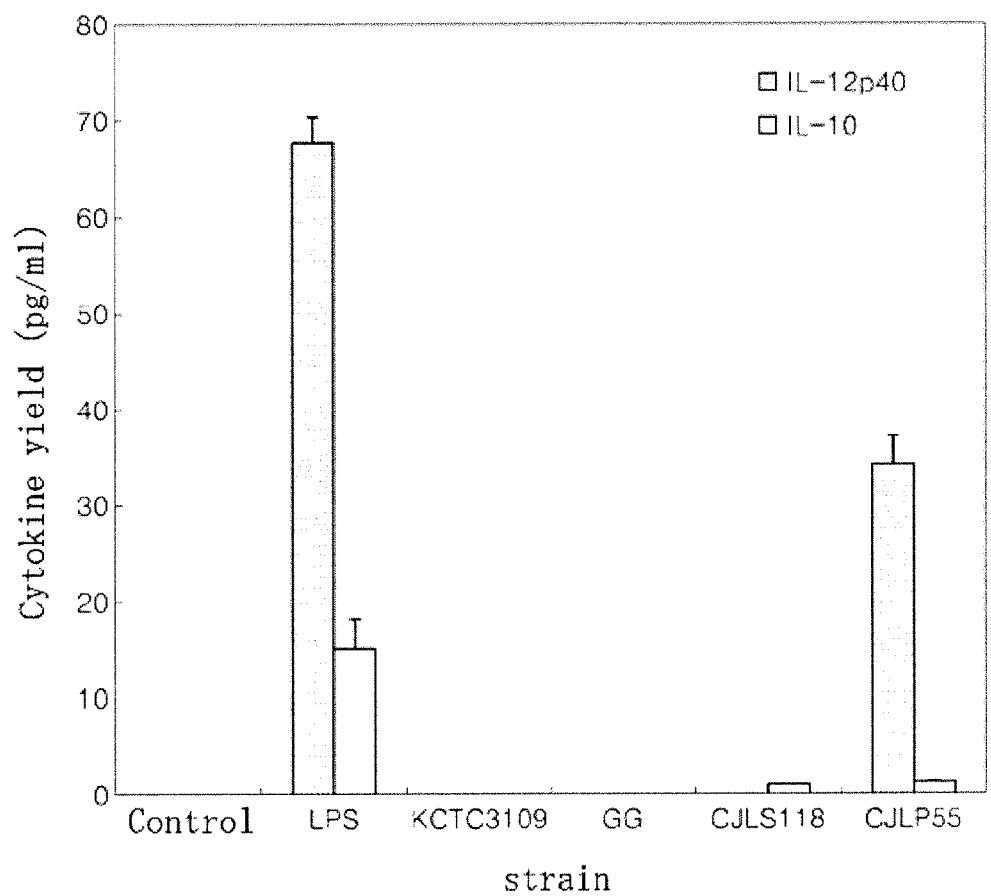
FIG. 7 is a graph showing the the concentrations of IL-12 and IL-10 produced in the dendritic cell line JAWSII treated with *Lactobacillus plantarum* CJLP55 or other lactic acid bacteria, as measured by ELISA.

FIG. 7 is a graph showing the concentrations of IL-12 and IL-10 produced in the dendritic cell line JAWSII treated with *Lactobacillus plantarum* CJLP55 or other references, as measured by ELISA.

As can be seen in FIGS. 6 and 7, *Lactobacillus plantarum* CJLP55 promotes the production of the Th1 differentiation-inducing cytokine IL-12, but shows the significantly less production of the Th1 differentiation-suppressing cytokine that of IL-12, and significantly increases the production of IL-12 compared to the other lactic acid bacteria.

To ascertain the production of IL-12 and IL-18 at the gene level, first, test bacteria were applied at a density of $5 \times 10^7$ cells/mL to the macrophage cell line RAW264.7 and, then, cultured at 37° C. for 6 hours in a 10% $CO_2$ incubator. Total RNA was isolated and used to determine the levels of IL-12 and IL-18 mRNA by RT-PCR. The dendritic cell line JAWSII was inoculated with the test bacteria, cultured and subjected to RNA isolation, followed by the determination of IL-12 and IL-18 mRNA levels by RT-PCR in the same manner as in the macrophages.

Figure 8:
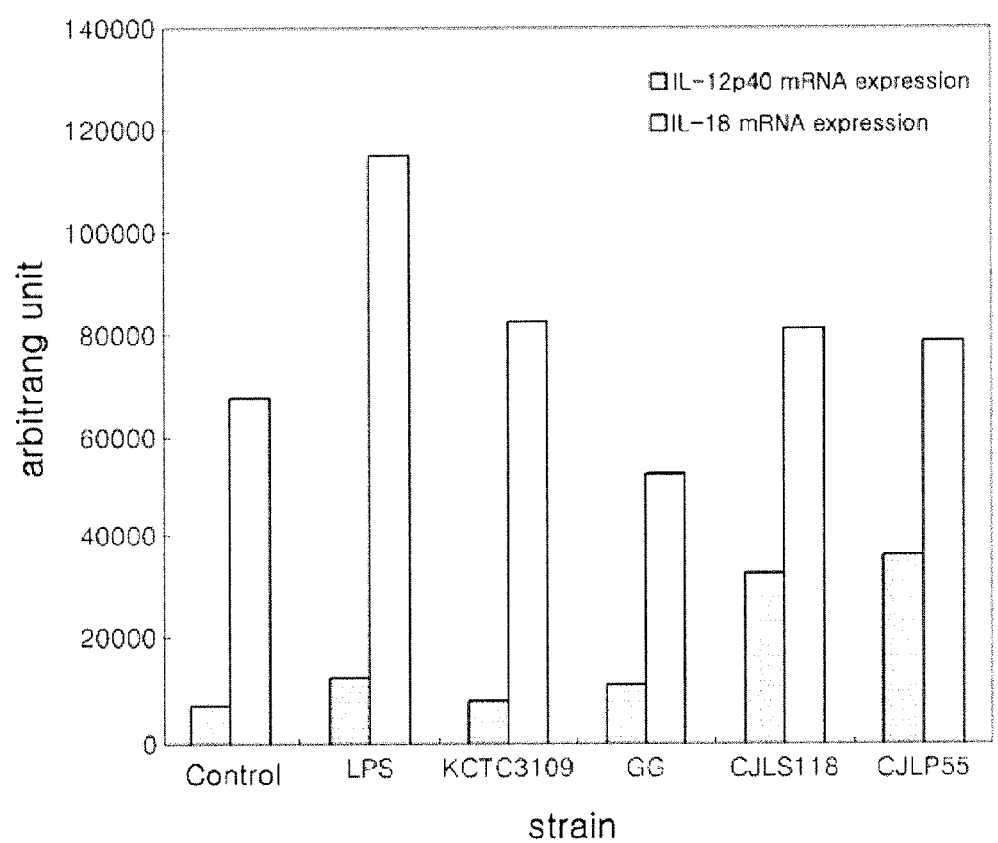
FIG. 8 is a graph showing the expression levels of IL-12p40 and IL-18 mRNA in the macrophage cell line RAW264.7 treated with *Lactobacillus plantarum* CJLP55 or other lactic acid bacteria, as measured by RT-PCR.
Figure 9:
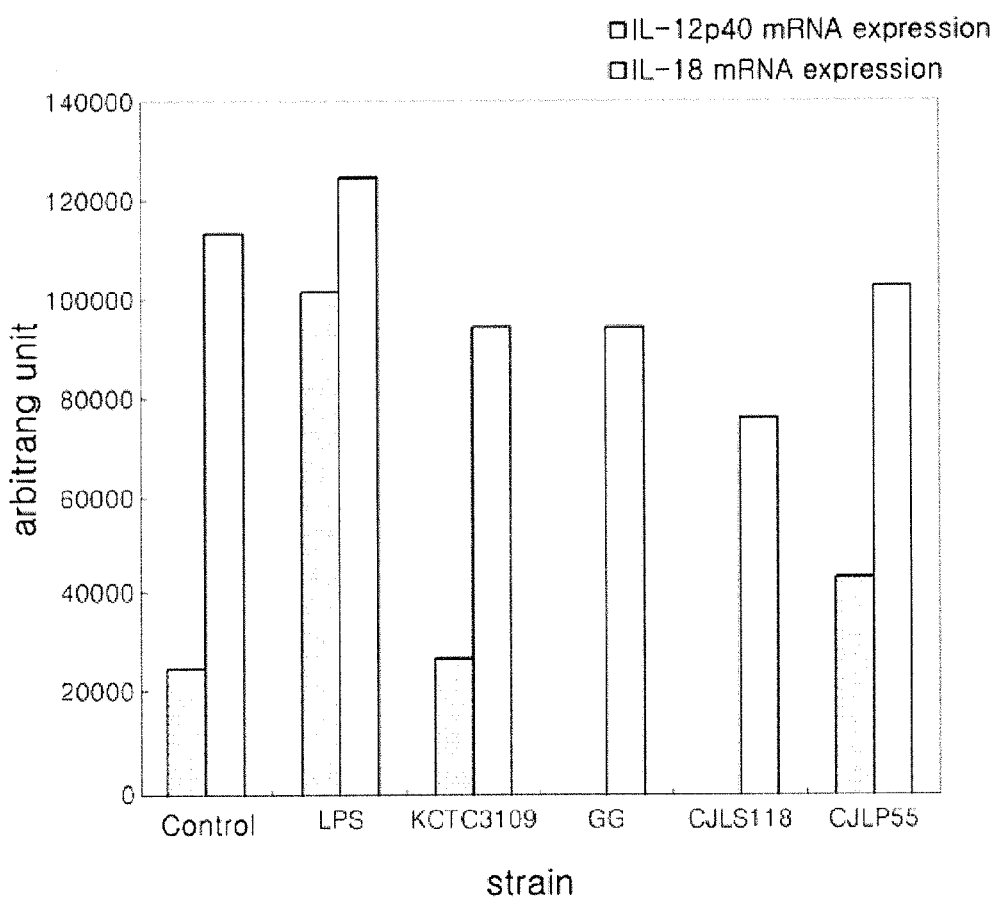
FIG. 9 is a graph showing the expression levels of IL-12p40 and IL-18 mRNA in the dendritic cell line JAWSII treated with *Lactobacillus* plantarum CJLP55 or other lactic acid bacteria, as measured by RT-PCR.

The results are shown in FIGS. 8 and 9, respectively.

FIG. 8 is a graph showing the expression levels of IL-12p40 and IL-18 mRNA in the macrophage cell line RAW264.7 treated with *Lactobacillus* plantarum CJLP55 or other references, as measured by RT-PCR.

FIG. 9 is a graph showing the expression levels of IL-12p40 and IL-18 mRNA in the dendritic cell line JAWSII treated with *Lactobacillus plantarum* CJLP55 or other references, as measured by RT-PCR.

As can be seen in FIGS. 8 and 9, *Lactobacillus plantarum* CJLP55 promotes the transcription of the mRNA which dictates the production of the Th1 differentiation-inducing cytokines IL-12 and IL-18.

EXAMPLE 8

Preparation of Probiotic Agent Comprising *Lactobacillus plantarum* CJLP55

The probiotic *Lactobacillus plantarum* CJLP55 identified in Example 1 was produced on a mass scale and lyophilized to make probiotics suitable for use as a raw material of pharmaceuticals, food, animal feed, feed additives or cosmetics.

The bacteria were incubated in MRS broth (Difco) at 37° C. for 18 hours while its pH was adjusted to 6.0 with a 25% NaOH solution, followed by harvesting the cells by centrifugation. The cells were frozen at −40 ° C. with 5% dextrin and 10% skim milk serving as cryoprotectants, and dried at 37° C. The cells thus lyophilized were powdered using a mixer. The powdered live bacteria were mixed with a suitable amount of an excipient such as glucose, lactose and skim milk for adjusting the number of bacteria to a desired level, and stored in a sealable aluminum pouch.

To be used in pharmaceuticals, food, animal feed, cosmetics and so on, the prepared probiotic agent may be mixed with grain powder used as a raw material of the animal feed, with an excipient or additive for pharmaceuticals in the form of tablets, capsules and so on, or with raw materials of cosmetics.

The invention claimed is:

1. A method for treating an immune disease caused by a Th1/Th2 imbalance in favor of a Th2 shift in a subject, comprising:
   administering a composition comprising *Lactobacillus plantarum* CJLP55 to the subject in need thereof.
2. The method of claim 1, wherein the composition is selected from the group consisting of pharmaceuticals, food, animal feed, feed additives and cosmetics.
3. The method of claim 1, wherein the subject is a human.
4. The method of claim 1, wherein the composition is administered orally.
5. A method for improving a microbial environment in a gastrointestinal tract of a subject, comprising:
   administering a composition comprising *Lactobacillus plantarum* CJLP55 to the subject in need thereof.
6. The method of claim 5, wherein the composition is selected from the group consisting of pharmaceuticals, food, animal feed, feed additives and cosmetics.
7. The method of claim 5, wherein the subject is a human.
8. The method of claim 5, wherein the composition is administered orally.
9. A method for treating an immune disease in a subject, comprising:

administering a composition comprising *Lactobacillus plantarum* CJLP55 to the subject in need thereof,
wherein the immune disease is caused by a Th1/Th2 imbalance in favor of a Th2 shift and is selected from the group consisting of allergic diseases, atopy, cancer, and enteropathy.

10. The method of claim 9, wherein the composition is selected from the group consisting of pharmaceuticals, food, animal feed, feed additives and cosmetics.

11. The method of claim 9, wherein the subject is a human.

12. The method of claim 9, wherein the composition is administered orally.

\* \* \* \* \*

SEQUENCE LISTING

<160> NUMBER OF SEQ ID NOS: 1

<210> SEQ ID NO 1
<211> LENGTH: 1457
<212> TYPE: DNA
<213> ORGANISM: Lactobacillus plantarum
<220> FEATURE:
<221> NAME/KEY: misc_feature
<222> LOCATION: (1436)..(1436)
<223> OTHER INFORMATION: n = g

<400> SEQUENCE: 1

```
agtcgaacga actctggtat tgattggtgc ttgcatcatg atttacattt gagtgagtgg      60
cgaactggtg agtaacacgt gggaaacctg cccagaagcg ggggataaca cctggaaaca     120
gatgctaata ccgcataaca acttggaccg catggtccga gtttgaaaga tggcttcggc     180
tatcactttt ggatggtccc gcggcgtatt agctagatgg tggggtaacg gctcaccatg     240
gcaatgatac gtagccgacc tgagagggta atcggccaca ttgggactga gacacggccc     300
aaactcctac gggaggcagc agtagggaat cttccacaat ggacgaaagt ctgatggagc     360
aacgccgcgt gagtgaagaa gggtttcggc tcgtaaaact ctgttgttaa agaagaacat     420
atctgagagt aactgttcag gtattgacgg tatttaacca gaaagccacg gctaactacg     480
tgccagcagc cgcggtaata cgtaggtggc aagcgttgtc cggatttatt gggcgtaaag     540
cgagcgcagg cggtttttta agtctgatgt gaaagccttc ggctcaaccg aagaagtgca     600
tcggaaactg ggaaacttga gtgcagaaga ggacagtgga actccatgtg tagcggtgaa     660
atgcgtagat atatggaaga acaccagtgg cgaaggcggc tgtctggtct gtaactgacg     720
ctgaggctcg aaagtatggg tagcaaacag gattagatac cctggtagtc cataccgtaa     780
acgatgaatg ctaagtgttg gagggtttcc gcccttcagt gctgcagcta acgcattaag     840
cattccgcct ggggagtacg gccgcaaggc tgaaactcaa aggaattgac ggggccccgc     900
acaagcggtg gagcatgtgg tttaattcga agctacgcga agaaccttac caggtcttga     960
catactatgc aaatctaaga gattagacgt tcccttcggg gacatggata caggtggtgc    1020
atggttgtcg tcagctcgtg tcgtgagatg ttgggttaag tcccgcaacg agcgcaaccc    1080
ttattatcag ttgccagcat taagttgggc actctggtga gactgccggt gacaaaccgg    1140
aggaaggtgg ggatgacgtc aaatcatcat gccccttatg acctgggcta cacacgtgct    1200
acaatggatg gtacaacgag ttgcgaactc gcgagagtaa gctaatctct taaagccatt    1260
ctcagttcgg attgtaggct gcaactcgcc tacatgaagt cggaatcgct agtaatcgcg    1320
gatcagcatg ccgcggtgaa tacgttcccg ggccttgtac acaccgcccg tcacaccatg    1380
agagtttgta acacccaaag tcggtggggt aaccttttag gaaccagccg cctaangtgg    1440
gacagatgat tagggtg                                                   1457
```